US008425862B2

(12) United States Patent
Thelu (10) Patent No.: US 8,425,862 B2
(45) Date of Patent: Apr. 23, 2013

(54) AUTOMATED SYSTEM FOR DETECTING THE FIXATION OF BIOMOLECULES ON A SAMPLE IN THREE DIMENSIONS (75) Inventor: Jacques Lucien Thelu, Crobes (FR)

(73) Assignees: Centre National de la Recherche Scientifique, Paris (FR); Universite Joseph Fourier, Saint-Martin d'Heres (FR)

( * ) Notice: Subject to any disclaimer, the term of this patent is extended or adjusted under 35 U.S.C. 154(b) by 1347 days.

(21) Appl. No.: 10/549,146

(22) PCT Filed: Mar. 4, 2004

(86) PCT No.: PCT/FR2004/000510
§ 371 (c)(1),
(2), (4) Date: Sep. 16, 2006

(87) PCT Pub. No.: WO2004/087953
PCT Pub. Date: Oct. 14, 2004

(65) Prior Publication Data
US 2007/0160496 A1    Jul. 12, 2007

(30) Foreign Application Priority Data
Mar. 20, 2003 (FR) ....................................... 03 03438

(51) Int. Cl.
*B01D 21/00* (2006.01)
(52) U.S. Cl.
USPC .............. 422/527; 422/67; 422/68.1; 422/82; 422/537; 436/177; 210/323.1; 210/418; 210/420

(58) Field of Classification Search ..................... 422/62, 422/67, 68.1, 81, 82, 99, 100, 102–105, 108–110, 422/116, 322, 323.1, 323.2, 418, 420, 424, 422/446, 527, 534, 535, 537, 608, 616, 236, 422/238; 436/177; 210/322, 323.1, 323.2, 210/418, 420, 424, 446
See application file for complete search history.

(56) References Cited

U.S. PATENT DOCUMENTS

| | | | | |
|---|---|---|---|---|
| 4,597,412 A | * | 7/1986 | Stark ............................ 137/606 |
| 4,776,962 A | * | 10/1988 | Wakeman ................ 210/748.01 |
| 5,225,080 A | * | 7/1993 | Karbachsch et al. ..... 210/321.75 |
| 5,250,263 A | * | 10/1993 | Manz ................................ 422/81 |
| 5,779,986 A | * | 7/1998 | van Endert et al. ........... 422/136 |
| 5,932,418 A | | 8/1999 | Yager |
| 2003/0049862 A1 | | 3/2003 | He et al. |

FOREIGN PATENT DOCUMENTS

| | | |
|---|---|---|
| WO | WO 02/23167 | 3/2002 |
| WO | WO 02/092778 | 11/2002 |

* cited by examiner

*Primary Examiner* — Lyle Alexander
(74) *Attorney, Agent, or Firm* — Young & Thompson

(57) ABSTRACT

The system has a plurality of dishes (1) for receiving at least one sample, each dish having a perforated base (2) enabling liquid reagents or solutions to pass continuously therethrough, the dishes being superposed in a confining tube (5); a circuit (50) for the continuous outflow of the solutions originating from distinct reservoirs (17); a multipath electrovalve (15); an electric pump (13); and a member for controlling and commanding the pump (13) and the multipath electrovalve (15) in a sequential and coordinated manner.

18 Claims, 2 Drawing Sheets

AUTOMATED SYSTEM FOR DETECTING THE FIXATION OF BIOMOLECULES ON A SAMPLE IN THREE DIMENSIONS

The present invention relates to an automated installation for detecting the fixation of molecules of biological origin or biomolecules on a sample in three dimensions, allowing in particular the location of the expression of genes or proteins by selective marking of these molecules in the mass of the sample by means of DNA or RNA probes, antibodies, enzymes or an appropriate combination of these markers.

In the prior art, a method is already known, which consists of selectively marking samples, generally thin sections which do not therefore allow overall observation of these samples and limit the interpretation of the results obtained by a marking of the latter, these measurements, which are moreover carried out manually, being lengthy, costly, and difficult to reproduce.

A method is also known for the selective marking of a structure in three dimensions in order to achieve a hybridization within the overall volume of a sample, in particular for detecting the expression of genes or also of an immunoreaction in the case of detection of proteins, this method known as hybridization "in toto" or "whole mount" being usually implemented by means of an automaton with an arm remotely controlled according to the three spatial dimensions.

But these apparatuses and their conditions of use are not very practical and above all do not have any great reliability, in particular due to the discontinuous execution of operations of successively filling and emptying the tubes or other receptacles individually containing the samples to be processed. Moreover, they are totally unsuitable when the solutions used as well as the reagents used must be placed under sufficient pressure to be able to penetrate to the core of the samples, especially if the latter are somewhat impermeable as is the case with most biopsies taken from living tissues.

A subject of the present invention is an automated installation which avoids these drawbacks thanks to the implementation of means which allow continuous detection under an appropriate pressure of the effects of a marking applied to a biological sample in three dimensions, in particular in order to obtain the expression of genes or proteins.

To this end, the installation considered is characterized in that it comprises:
- a plurality of modules in the form of individual dishes for receiving one or more samples to be treated, each comprising a side wall closed by a perforated base for the continuous passage inside the dish of solutions or liquid reagents to be brought into contact with the sample, these dishes having the same diametral space requirement and being accommodated in vertical superposition in a tube or a similar external positioning and confining casing,
- a circuit for the continuous flow through the dishes into the confining tube, under adjustable pressure, of these solutions, originating from distinct reservoirs, these solutions being introduced on demand, together or separately into this circuit,
- a multipath solenoid valve, suitable for separately connecting each solution reservoir with the circuit,
- an electric pump, preferably reversing the pumping and delivery direction, capable of effecting the continuous circulation in the circuit of the quantities of solutions taken from the reservoirs,
- and a sequential and coordinated control and command means of the pump (13) and of the multipath solenoid valve.

The installation circuit can be a closed loop circuit, for the permanent recycling of the solutions or open, for the removal of these solutions after at least one passage through the dishes in the confining tube.

Preferably, the dishes are stacked in the confining tube arranged vertically, with the solutions flowing upwards in the tube.

According to another characteristic, the installation comprises a second multipath solenoid valve, allowing either the recovery of at least some of the solutions in order to cause them to circulate in a loop in the circuit, before returning them to their respective reservoirs or the removal of these solutions to an external evacuation receptacle.

Advantageously, the dishes for receiving the samples are cylindrical and have the same height from one dish to another. As a variant however, the dishes can have different heights, in particular depending on the size and space requirement of the samples contained in these dishes.

According to a particular characteristic, the dishes for receiving the samples, stacked in the confining tube, are immobilized between a fixed lower base, closing this tube, and a mobile upper base, the displacement of which inside the tube in order to be applied to the stack of dishes, is controlled by an actuation piston outside this tube, plunging into the latter and comprising an axial channel for the circulation of the solutions in the circuit.

Preferably, the mobile base is equipped with a tight scraper, made of an appropriate elastic material, bearing against the internal surface of the confining tube in order to avoid the leakage of liquid solutions out of this tube.

Also advantageously, the side wall of each dish is transparent and made of a plastic material, in particular a polymer such as polystyrene, methyl methacrylate or polycarbonate.

In a preferred embodiment, the base of each dish is moreover constituted by a fine-meshed sieve, in particular made of polyester or "Nylon" cloth.

According to another characteristic, the confining tube is made of glass or a transparent plastic material.

According to yet another characteristic, the sequential control and command means comprise a micro-computer which determines the composition, the order of their flow in the circuit and the period for which the solutions or reagents are brought into contact with the samples in the dishes, as well as the flow rate of these solutions.

In a preferred embodiment, the confining tube is accommodated in a thermostatically controlled and thermoregulated enclosure.

Advantageously, this thermostatically-controlled enclosure comprises a metallic strip, glued or otherwise applied to a generatrix of the confining tube, this strip being maintained in contact with a block of solid metal, against which is mounted an element suitable for achieving controlled heating of this block.

Preferably also, the circuit comprises a coil sealed in the metal block, placed in series in this circuit upstream from the confining tube, such that the solutions or reagents passing through the stacked dishes are taken to the regulated temperature of this metal block. In particular, the coil can be made of stainless steel and the metal block of aluminium.

Usefully, the confining tube and the metallic strip are surrounded by a protective cover, preferably made of plastic.

Thanks to these various arrangements, implemented together or separately depending on the case, the invention makes it possible to subject the samples in three dimensions placed in the modules formed by the dishes superposed inside the confining tube, to a continuous flow of solutions or reagents, avoiding any requirement for the intermittent renewal of the latter, in particular with successive filling and emptying cycles as in the prior embodiments.

The installation proposed, on the other hand, allows complete automation of the method, thanks to the use of the electric pump and multipath solenoid valve, as well as the coordinated control of these apparatuses by the micro-computer.

This continuous flow of the reagent solutions in particular has the effect of increasing the effectiveness of their transfer to the very core of the samples contained in the dishes, with neither exhaustion nor stagnation of these reagents in contact with these samples. This avoids their deposit being superficial and provides increased effectiveness of their penetration to the core of the sample with overall shorter stages.

The installation is moreover tight, which is a real advantage in the case of the use of samples the nature of which requires that they should be confined. Moreover, the electric pump can be used at variable pressures, in particular greater than atmospheric pressure, in order to increase the transfer of the solutions or reagents to the core of these samples, even if the latter have a certain impermeability, due for example to a considerable cell differentiation.

Similarly, thanks to the use of a relatively high pressure in the circuit, it is possible to analyze in depth certain samples having a low penetrability vis-à-vis the reagents used, in particular such as biopsies.

The installation also has the advantage that each sample can be treated in the latter in an appreciably identical and perfectly reproducible manner, experience showing that in a permanent flow of solutions or reagents, the reciprocal interferences of the treatment conditions of one sample with another in successive dishes are compensated for by the dynamics of this flow which constantly renews and homogenizes the environment of these samples and does not affect the results of measurements carried out on each of them.

The installation according to the invention allows continuous recycling, in this case preferably in a closed loop, of the most expensive liquid reagents such as DNA or RNA probes, or antibodies, these reagents thus being able to be recycled and used in a more dilute manner than in the case of a static method, the molecules having a particular affinity being moreover trapped solely in the zone specific to the sample.

This installation can be adjusted at will and can bring into play a number of variable samples, the dimensions of the system being easily adapted to the number of dishes, in particular using the mobile piston and tight scraper which it comprises.

It is finally designed to provide precise thermoregulation of the conditions under which the marking of the samples and the measurements are carried out, without thermal shock to the solutions and reagents recently taken from the reservoirs and introduced into the circuit, thanks to the circulation of these solutions in the coil buried in the metal block, before their passage into the tube through the stacked dishes.

Thus the installation makes it possible to modify the temperature adopted according to the user's wishes, it being possible to carry out most of the incubations at ambient temperature, unlike the hybridization stages which must most generally be carried out at a higher stable temperature, of the order of 70°.

The introduction of the samples and dishes into the installation and their withdrawal from it are very easy, being able to be carried out simply, in particular by means of a clamp or similar tool through the end of the tube after removal of its top mobile base, the use of a tube of transparent material providing satisfactory visibility.

During the introduction of the dishes, the perforated, very fine-meshed base of which is difficult for air to pass through, it is possible to avoid trapping the latter between two successive dishes during the introduction of the latter into the tube, the bubble formed being likely to subsequently falsify the measurements. To this end, it is sufficient to momentarily reverse the flow of the solutions by the pump in order to compensate for the rising of the liquid induced by the introduction of these dishes, before the stacking of the latter in a sufficient number is immobilized by the piston acting on the mobile base and the tight scraper applied to the top dish in this stack; the movement of the pump is then reversed in order to return to the normal direction of circulation of the solutions and reagents in the tube, in particular from the bottom to the top in the latter.

For the withdrawal of the samples, it is sufficient to proceed in the opposite manner by first withdrawing the piston, then introducing an appropriate quantity of air through the base of the tube after having drained the connection between the pump and any reservoir of solution. The air bubble which forms in this case at the base of the tube progressively pushes the dishes upwards under the effect of the pumping, making it possible to recover the dishes and the samples contained in the latter one by one.

Other advantages and characteristics of the installation considered will also become apparent through the description which follows of an embodiment of the latter, explained with reference to the attached drawings, as well as several examples of protocols which can be used with this installation, these protocols being provided solely for information and non-limitatively.

Figures 1, 2, 3:
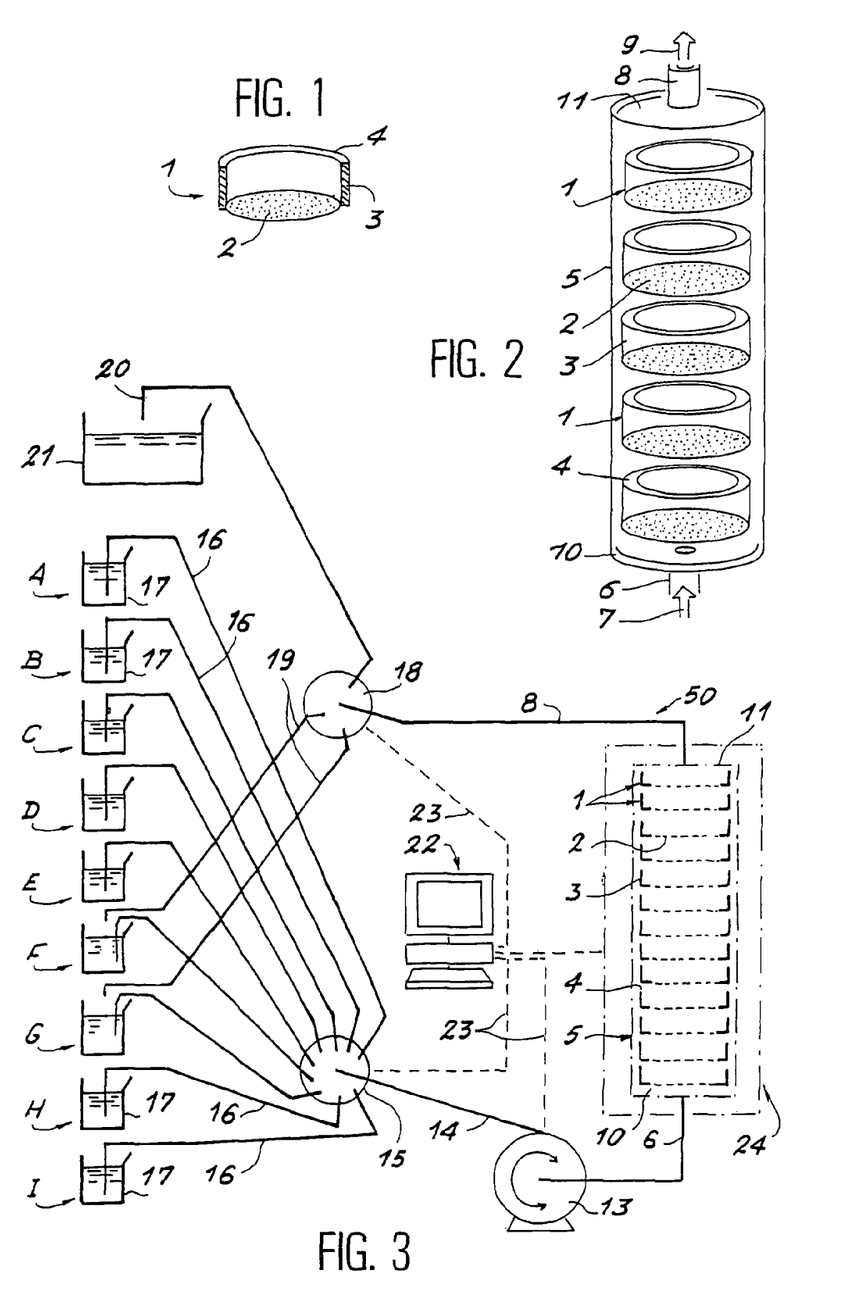
FIG. 1 is a perspective view and partial axial cross-section of a dish forming part of the embodiment of the installation considered.
FIG. 2 is an exploded perspective view of the confining tube of a stack of dishes used in the installation.
FIG. 3 is a general diagram of the installation.

In FIG. 1, the dish shown, designated in its entirety by the reference 1, is made up of a perforated base 2, preferably formed by a cloth made of "Nylon" (registered trademark) or a similar plastic material, the mesh size of which is chosen in order to allow the free flow of an appropriate liquid flow through this base, without excessive pressure drop, the cloth moreover having sufficient mechanical resistance to make it possible to house and support inside the dish, a sample in three dimensions, on which it is desired to carry out a marking by a probe, an antibody or an enzyme, or any other suitable selective element.

The dish 1 moreover comprises a side wall 3 generally cylindrical in shape in the example shown, but the section of which could be different, this wall being joined by any suitable bonding method to the peripheral edge of the cloth of the base 2. The dish is completely open at its end 4 opposite this base.

FIG. 2 illustrates very diagrammatically, in exploded view, the assembly of a set of dishes 1 of the type described above, these dishes being provided in order to be superposed on each other continuously inside a confining tube 5.

This tube 5 is advantageously made of "Pyrex" (registered trademark) type glass, having an appropriate thickness, generally of the order of 5 mm in order to have a suitable resistance vis-à-vis the internal pressure of the solutions as well as any impacts during handling, while however ensuring a good heat exchange with a temperature control assembly described below, or constituted by a transparent plastic, in particular a polymer of the polystyrene, methacrylate or polycarbonate type, making it possible to see the stack of dishes 1 inside this tube.

The cross-section of the latter is more or less equal to that of the dishes 1, in such a manner that a flow of an appropriate liquid solution, the nature of which will be indicated below, introduced at the base of the tube 5 through a lower connecting channel 6, in particular in the upward direction represented by the arrow 7, the tube being arranged vertically, passes completely through each of the dishes 1 in the stack in order to be finally taken up in the top part through an evacuation channel 8, in the direction of the arrow 9.

The confining tube 5 is closed at its bottom end by a fixed base 10, into which the connecting channel 6 opens, and comprises at its top end a mobile base 11 via a piston 12 (not shown) in FIG. 2, but which appears in FIG. 4, this piston resting on the stack of the dishes 1 in the tube 5 fixing each of them on those situated below.

FIG. 3 illustrates the whole of the installation in greater detail, though diagrammatically.

The connecting channel 6 to the confining tube 5 is connected to an electric pump 13, being able, according to the case, to suck in or force back the liquid solution which circulates through the stack of the dishes 1.

This pump 13 is connected by a pipe 14 to a multipath solenoid valve 15, connecting this pipe 14 to a tubular connection piece such as 16, mounted between one of the outlets of this solenoid valve and a solution reservoir 17.

In the embodiment example represented, the installation comprises nine tubular connection pieces 16 and nine reservoirs 17, each containing a different solution or liquid reagent, these nine reservoirs being denoted in the figure by the references A to I. Nine tubular pieces 16 thus connect the pump 15 to the nine reservoirs 17.

The outlet channel 8, at the top part of the confining tube 5, is connected to a second multipath solenoid valve 18, making it possible, in the example illustrated, to select one of three positions.

Under these conditions, this solenoid valve 18 can connect the outlet channel 8 from the tube 5 by a tubular piece 19 to two given reservoirs 17, here the reservoirs F and G, in order to form with the tube 5, the channel 6, the pump 13 and the pipe 14, a closed circuit, in a closed loop, generally designated by the reference 50, and in which the solution or the reagent originating from the reservoir 17 thus selected in the first two positions of the solenoid valve 18 circulate.

As a variant, for the third position of the multipath solenoid valve 18, the solution originating from any one of the reservoirs 17 through its associated tubular piece 16, after circulation in the circuit 50 and in particular in the confining tube 5, is returned through a pipe 20 towards an evacuation container 21, in particular if this solution is unsuitable for reuse.

The control of the positions of the solenoid valves 15 and 18, according to the arrangement chosen for the tubular pieces 16 and 19, makes it possible to modify at will the choice of the solutions contained in the reservoirs 17 and the circulation of the latter in a closed-loop or open circuit with removal of these solutions after use when it is not necessary to recycle them.

The control of the operation of the electric pump 13, in particular its pumping direction, and that of the multipath solenoid valves 15 and 18, is ensured by a micro-computer 22, from which the connections 23 for controlling these apparatuses start, the electrical connections not being shown in order not to overload the diagram.

Figure 4:
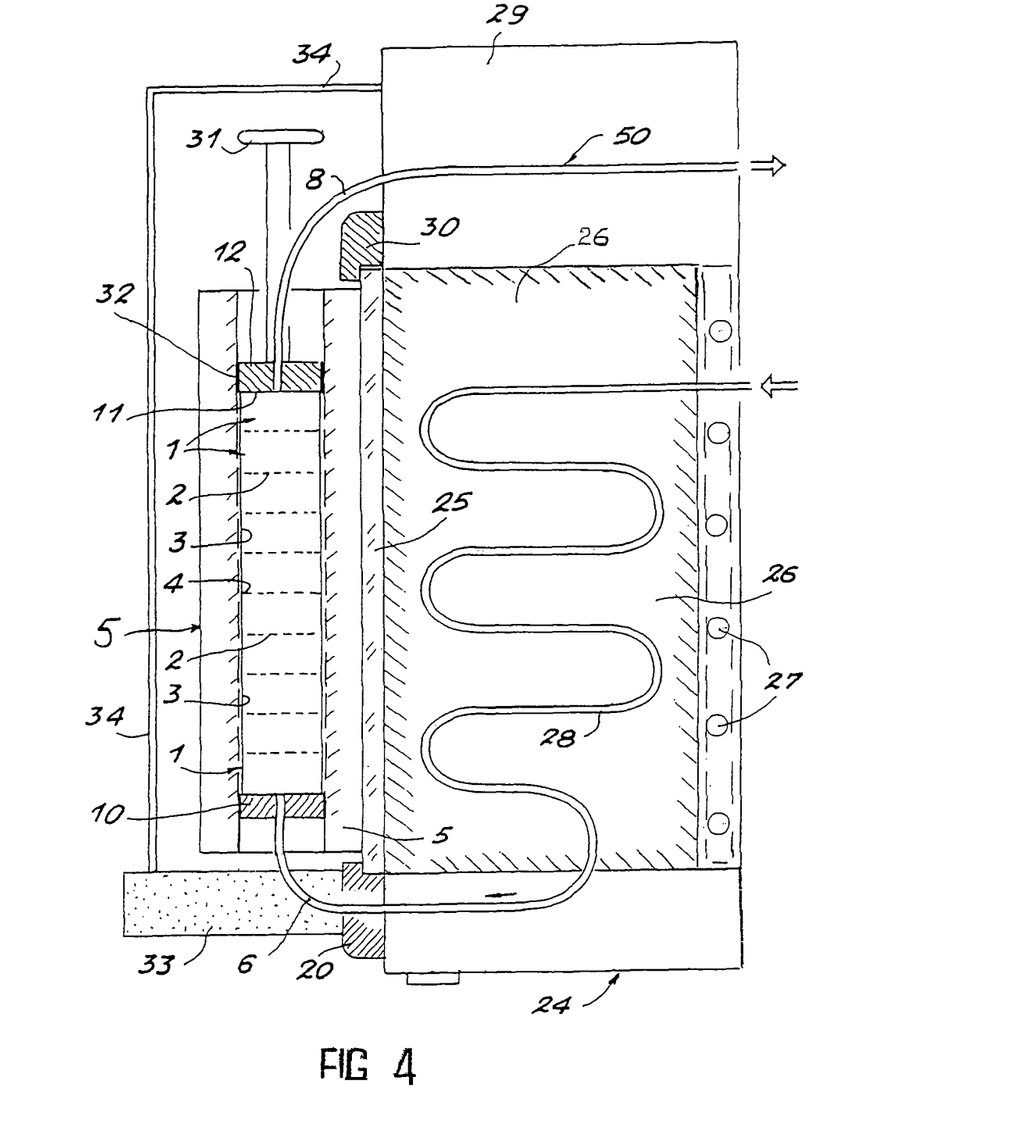
FIG. 4 is also a diagrammatic cross-section of an embodiment of the confining tube of the dishes and of the thermostatically controlled enclosure associated with it.

In FIG. 3, the reference 24 finally designates a thermostatically controlled and thermoregulated enclosure in its entirety, shown very diagrammatically, advantageously provided in the installation considered, the design of which appears in more detail in FIG. 4.

The confining tube 5 comprises a lateral metal strip 25, glued or fixed to the outside by other appropriate means against a vertical generatrix of this tube, this strip itself being in contact with a metal block 26, to which a heating resistor 27 is fixed. The strip and the block are preferably made of aluminium.

The connecting channel 6 which passes through the fixed base 10 of the confining tube 5 is joined to a coil 28, advantageously made of stainless steel, fixed and applied against the metal block 26 in such a manner that the solution or the liquid reagent which passes through the circuit 50 is permanently brought to the regulated temperature of the block. The enclosure 24 is mounted in an outer protective and insulating casing 29.

In FIG. 4, the mobile base 11 at the top part of the confining tube 5, above the stack of dishes 1, is in contact with the piston 12, which is extended by a control rod 31 making it possible to manoeuvre it inside the tube and to apply it to the top dish. The piston 12 comprises laterally a scraper 32 made of an elastic material, ensuring the tightness of the assembly and in particular of the stack of dishes 1 inside the confining tube 5.

The evacuation channel 8 passes through the piston 12 in order to open into the tube 5 and allows the circulation of the solution in the circuit 50.

The confining tube 1 is applied to the block 26 and held by locking means 30, advantageously arranged at the top and bottom ends of the strip 25. The tube 5 and the piston 12 are housed in a lateral extension 34 of the casing 29, forming a protective cover, the latter being closed at the low part by an insulating support 33.

The installation thus designed makes it possible to carry out, in an automated and continuous fashion, if appropriate under appropriate pressure and at a desired temperature, the marking of biological samples in three dimensions, with antibody probes or enzymes or also by a combination of these markers, the micro-computer 22 permanently ensuring the control and management of the operations carried out, by modifying in each particular case the nature of the solution to be used, the time for passing this solution over these samples, the marking conditions and recording the results obtained. It also makes it possible to control in the same manner, after each passage of solution and/or marking of a sample, the phases which may be necessary of rinsing the circuit before implementing a new analysis.

The examples given below indicate the protocols to be followed in the different cases taken into consideration.

EXAMPLE 1

Specific detection of the messenger RNAs transcribed from the Wnt-11 gene. These messenger RNAs reveal the action of the Wnt-11 gene on chicken embryos at 3 and 4 days of development. This protocol makes it possible to directly visualize on the sample (embryo) the activation locus of the gene, this activation of Wnt-11 revealing the first stage of the formation of the dermis of the skin.

Reagents

A—50 ml of ethanol intended to place the sample in the same solvent as that of a storage previously carried out at −20° C. (designated Et OH).

B—50 ml of phosphate buffer (Phosphate Buffer Saline PBS), pH=7.2 and 50 µl of Tween 20 detergent, intended to progressively rehydrate the sample whilst preserving the isotonicity and the physiological pH necessary for the proper functioning of the reagents used subsequently.

The detergent is intended to facilitate the transit of the reagents within the sample (designated PBT).

C—10 µl of proteinase K (at 10 mg/ml) in 10 ml of reagent B. This enzyme is intended to partially permeabilize the sample, by degrading certain membrane proteins, in order to improve the penetration within the sample of the reagents used subsequently (designated Pro K).

D—Fixer: 5.4 ml of 37% formaldehyde; 200 µl of 0.5 M EDTA (ethylene diamine tetra acetate); 50 µl of 1M soda, a quantity sufficient for 50 ml of PBS. The fixer is intended to consolidate the sample which has been partially made fragile by proteinase K (designated Fix).

E—25 ml of formamide, 12.5 ml of SSC 20× (Sodium Saline Citrate) buffer, 12.5 ml of water, 50 µl of Tween 20. This pre-hybridization solution is intended to place the sample under ideal conditions promoting the specific hybridization of the single-strand RNA probe on the transcribed messenger RNA in the cells of the sample (designated Mix).

F—5 µl of probe (Wnt-11), constituted by a single-strand anti-sense messenger RNA, obtained by the transcription of a double-strand DNA coding for the Wnt-11 protein. This DNA is itself obtained beforehand by molecular recombination and amplification within a bacterial plasmid. The anti-sense messenger RNA is marked during its synthesis using nucleotides chemically coupled to digoxigenin DIG. The digoxigenin here plays the role of the hapten, or peptide which can be recognized and specifically bound by an antibody; 5 ml of reagent E (designated Probe).

G—4 ml of reagent B, 1 ml of serum, 5 µl of monoclonal antibody of murine origin, directed specifically against digoxigenin (DIG) and coupled to the alkaline phosphatase enzyme, marketed by Roche (designated Ac).

H—NTMT buffer, intended to alkalize the medium and made up of 1 ml of 5 M NaCl, 2.5 ml of 1M MgCl2, 2.5 ml of 2M Tris HCl pH 9.5, 50 µl of Tween 20 detergent in a quantity sufficient for 50 µl of water.

I—NBT/BCIP reagent, intended to reveal the alkaline phosphatase enzyme activity by producing insoluble violet staining, 2.4 mg of levamisol, 1 NBT/BCIP tablet, 10 ml of water.

Programme

The reagents are injected into the system, with a continuous flow rate of 1 ml per minute, according to the following sequence:

A+B: 15 mn, continuous gradient of aqueous solution of PBT (rehydration)
B: 10 mn, washing with PBT buffer
C: 7 mn, permeabilization with proteinase K.
B: 5 mn, washing with PBT buffer
D: 15 mn, fixing of the samples with formaldehyde
B: 5 mn, washing with PBT buffer
E: 15 mn, pre-hybridization with a solution of formamide and SSC; gradual temperature increase to 70° C.
F: 360 mn, hybridization with the anti-sense RNA probe, Wnt-11 (continuous recycling) at 70° C.
E: 15 mn, washing with a solution of formamide and SSC; gradual temperature reduction to ambient.
B: 45 mn, washing with PBT buffer
G: 360 mn, complexing of the anti-DIG antibody (continuous recycling)
B: 120 mn, washing with PBT buffer
H: 10 mn, balancing of the samples with buffer pH=9.5
I: 120 mn, development by the TNBT/BCIP substrate.

Results

Only the areas of the embryo where the Wnt-11 gene is activated (expression domains) are stained violet. In this specific case, these areas correspond to the dorsal medial lip of the dermomyotome of the somites. The staining obtained defines a dotted area, situated on either side of the neural tube, revealing precursor cells, at the origin of the formation of the dermis and which, after successive divisions, will colonize the embryo in order to take part in the formation of skin.

EXAMPLE 2

Specific detection of the messenger RNAs transcribed from the Msx-1 gene. This example is similar to Example 1; however the protocol is simplified in that the first stage of rehydration of the samples is already carried out. The last revelation stage is carried out outside the apparatus in such a manner that the experimenter can stop the reaction at the desired moment, as a function of the intensity of the desired staining.

The Msx-1 anti-sense RNA probe reveals the activation of the Msx-1 gene on chicken embryos at 3 and 4 days of development. This protocol makes it possible to directly visualize on the sample (embryo) the activation locus of the gene, this activation of Msx-1 revealing the formation of the skin and limb buds.

Reagents

B—500 ml of phosphate buffer (Phosphate Buffer Saline PBS) pH=7.2 and 500 µl of Tween 20 detergent, intend to preserve the isotonicity and the physiological pH necessary for the proper functioning of the reagents used subsequently. The detergent is intended to facilitate the transit of the reagents within the sample (designated PBT).

C—60 µl of proteinase K (at 10 mg/ml) in 30 ml of reagent B. This enzyme is intended to partially permeabilize the sample by degrading certain membrane proteins, in order to improve the penetration within the sample of the reagents used subsequently (designated Pro K).

D—Fixer 5.4 ml of 37% formaldehyde, 200 µl 0.5 M EDTA (Ethylene Diamine Tetra Acetate), 50 µl of 1M soda, a quantity sufficient for 50 ml PBS. The fixer is intended to consolidate the sample which has been partially made fragile by proteinase K (designated Fix).

E—25 ml of formamide, 12.5 ml of SSC 20× (Sodium Saline Citrate) buffer, 12.5 ml of water, 50 µl of Tween 20. This pre-hybridization solution is intended to place the sample under ideal conditions promoting the specific hybridization of the single-strand RNA probe on the transcribed messenger RNA in the cells of the sample (designated Mix).

F—5 µl of probe (Msx-1) constituted by a single-strand anti-sense messenger RNA, obtained by the transcription of a double-strand DNA coding for the Msx-1 protein. This DNA is itself obtained beforehand by molecular recombination and amplification within a bacterial plasmid. The anti-sense messenger RNA is marked during its synthesis using nucleotides chemically coupled to digoxigenin DIG. The digoxigenin here plays the role of the hapten, or peptide which can be recognized and bound specifically by an antibody; 5 ml of reagent E (designated probe).

G—4 ml of reagent B, 1 ml of serum, 5 µl of monoclonal antibody of murine origin specifically directed against digoxigenin (DIG) and coupled to the alkaline phosphatase enzyme, marketed by Roche (designated Ac).

H—NTMT buffer intended to alkalize the medium and made up of 1 ml of 5M NaCl, 2.5 ml of 1M MgCl2, 2.5 ml of 2M Tris HCl pH 9.5, 50 µl of Tween 20 detergent in a sufficient quantity for 50 ml of water.

Programme

The reagents are injected into the system, at a continuous flow rate of 1.5 ml per minute, according to the following sequence:

B: 10 mn, washing with PBT buffer
C: 12 mn, permeabilization with proteinase K.
B: 5 mn, washing with PBT buffer
D: 15 mn, fixing of the samples with formaldehyde.
B: 5 mn, washing with PBT buffer
E: 20 mn, pre-hybridization with a solution of formamide and SSC; gradual temperature increase to 70° C.
F: 8 hours, hybridization with the anti-sense RNA probe, Wnt-11 (continuous recycling) at 70° C.
E: 20 mn, washing with a solution of formamide and SSC; gradual temperature reduction to ambient.
B: 45 mn, washing with PBT buffer
G: 7 hours, complexing of the anti-DIG antibody (continuous recycling)
B: 2 hours, washing with PBT buffer
H: 10 mn, balancing of the samples with buffer pH=9.5

Results

Only the areas of the embryo where the Msx-1 gene is activated (expression domains) are stained violet. In this specific case, these areas correspond to the dorsal part of the neural tube as well as to the AER (apical ectodermal ridge) of the limb buds.

EXAMPLE 3

Specific detection of the Myo-D proteins present in the muscle precursor cells.

This example is based on an exclusively immunological revelation of the presence of a protein (Myo-D) using a specific antibody.

In summary, the monoclonal antibody of murine origin directed against the Myo-D protein is then itself recognized and bound to a secondary antibody (mouse anti-immunoglobin) itself marked by a covalent bond to an enzyme: peroxidase.

Reagents

B—700 ml of phosphate buffer (Phosphate Buffer Saline PBS) pH=7.2 (700 μl of Tween 20 detergent, intended to wash the sample while preserving the isotonicity and the physiological pH necessary for the proper functioning of the reagents used subsequently. The detergent is intended to facilitate washing and the transfer of the reagents within the sample (designated PBT).

F—5 μl of monoclonal antibody directed specifically against the Myo-D protein diluted in 10 ml of reagent B (designated primary antibody).

G—5 μl of polyclonal antibody directed specifically against mouse immunoglobulin marked by conjugation to an enzyme, peroxidase.

The antibody is diluted in 10 ml of reagent B (designated secondary antibody).

Programme

The reagents are injected into the system, at a continuous flow rate of 1.5 ml per minute, according to the sequence defined as follows:

B: 30 mn, balancing of the samples under physiological conditions
F: 8 hours 30 mn, complexing of the primary antibody under continuous recycling.
B: 2 hours, washing of the samples in order to remove the molecules bound in non-specific manner.
G: 8 hours, complexing of the secondary antibody under continuous recycling B: 3 hours, washing of the samples in order to remove the molecules bound in non-specific manner.
B: washing under continuous recycling
Revelation of the enzyme activity by diaminobenzidine (DAB).

Results

Only the areas of the embryo where the Myo-D protein is expressed (i.e. present) are stained brown. In this specific case, these areas correspond to the dermomyotome of the somites as well as to all the areas where the muscles are becoming established in the embryo at this stage.

EXAMPLE 4

Automation of the apparatus makes it possible to carry out tasks such as purging the tubes in order to refill them with the different reagents used. For example, by going back to Example 1.

Reagents

A—50 ml of ethanol intended to place the sample in the same solvent as that of storage which was previously carried out at −20° C. (designated Et OH).

B—50 ml of phosphate buffer (Phosphate Buffer Saline PBS), pH=7.2 and 50 μl of Tween 20 detergent, intended to progressively rehydrate the sample whilst preserving the isotonicity and the physiological pH necessary for the proper functioning of the reagents used subsequently. The detergent is intended to facilitate the transit of the reagents within the sample (designated PBT).

C—10 μl of proteinase K (at 10 mg/ml) in 10 ml of reagent B. This enzyme is intended to partially permeabilize the sample, by degrading certain membrane proteins, in order to improve the penetration within the sample of the reagents used subsequently (designated Pro K).

D—Fixer: 5.4 ml of 37% formaldehyde; 200 μl of 0.5 M EDTA (ethylene diamine tetra acetate); 50 μl of 1M soda, a quantity sufficient for 50 ml of PBS. The fixer is intended to consolidate the sample which has been partially made fragile by proteinase K (designated Fix).

E—25 ml of formamide, 12.5 ml of SSC 20× (Sodium.Saline Citrate) buffer, 12.5 ml of water, 50 μl of Tween 20. This pre-hybridization solution is intended to place the sample under ideal conditions promoting the specific hybridization of the single-strand RNA sample on the transcribed messenger RNA in the cells of the sample (designated Mix).

F—5 μl of probe (Wnt-11), constituted by a single-strand anti-sense messenger RNA, obtained by the transcription of a double-strand DNA coding for the Wnt-11 protein. This DNA is itself obtained beforehand by molecular recombination and amplification within a bacterial plasmid. The anti-sense messenger RNA is marked during its synthesis using nucleotides chemically coupled to digoxigenin DIG. The digoxigenin here plays the role of the hapten, or peptide which can be recognized and specifically bound by an antibody; 5 ml of reagent E (designated Probe).

G—4 ml of reagent B, 1 ml of serum, 5 μl of monoclonal antibody of murine origin, directed specifically against digoxigenin (DIG) and coupled to the alkaline phosphatase enzyme, marketed by Roche (designated Ac).

H—NTMT buffer, intended to alkalize the medium and made up of 1 ml of 5 M NaCl, 2.5 ml of 1M MgCl2, 2.5 ml of 2M Tris HCl pH 9.5, 50 μl of Tween 20 detergent in a quantity sufficient for 50 ml of water.

I—NBT/BCIP reagent, intended to reveal the alkaline phosphatase enzyme activity by producing insoluble violet staining, 2.4 mg of levamisol, 1 NBT/BCIP tablet, 10 ml of water.

Programme

The reagents are injected successively into the system, at a continuous flow rate of 1 ml per minute, at the rate of 15 seconds for each reagent.

Results

This period is necessary and sufficient to fill the tubular pieces (dead volume) corresponding to each reagent. Therefore the system is ready for an analysis programme without the risk of injecting air or water from a previous rinsing.

EXAMPLE 5

The automation of the apparatus makes it possible to simply carry out complete rinsing of the installation at the end of the experiment. For this purpose the receptacles containing the reagents are filled with water whilst a specific programme then carries out this rinsing.

Programme

The water is injected successively into the circuit, with a continuous flow rate of 1.5 ml per mn, at a rate of 10 mn for each feed connection piece of a reagent.

Results

This period is necessary but sufficient to carefully rinse the tubular pieces, pipes and other accessories of the installation where each reagent has circulated. Then the assembly is ready for a new analysis programme.

Thus an adjustable and automated installation is produced for the detection of a marking on molecules of biological origin, of very simple and inexpensive design, easy to use and highly efficient, in particular for the treatment of samples in three dimensions.

In particular, this installation with the confining tube containing the dishes and the loop circuit for the circulation of the solutions and liquid reagents, can be miniaturized and made relatively compact, allowing, by the thermostatically controlled and thermoregulated enclosure, precise control of the operating temperature. The use of a control and command micro-computer in order to control the operation can be carried out in a standard "Windows"-type (registered trademark) environment, making it possible to create or modify analysis programmes and store them in memory.

Of course, it goes without saying that the invention is not limited to the embodiment more especially described and diagrammatically shown in the attached drawings; on the contrary, it covers all variations.

The invention claimed is:

1. An automated installation for detecting fixation of molecules of biological origin or biomolecules on a sample in three-dimensions, comprising:
 a plurality of individual containers (1), each of the containers having an internal empty space for receiving a respective different three-dimensional sample to be treated at a same time, each of the containers comprising a perforated base (2) and a side wall (3) defining the internal empty space, the side wall being distinct from and closed by the perforated base (2) for the continuous passage inside the respective containers of solutions or liquid reagents to be brought into contact with the sample, these containers having the same diametric space requirement and being accommodated in vertical superposition in an external casing positioning and confining the containers, the perforated base comprising a cloth with a mesh size allowing free flow of the solutions or liquid reagents, the cloth being arranged to house and support the respective sample in the respective one of the containers,
 a circuit (50) for the continuous flow through the containers (1) into the casing, under adjustable pressure, of these solutions or liquid reagents, originating from distinct reservoirs (17), these solutions or liquid reagents being introduced on demand, together or separately into this circuit,
 a multipath solenoid valve (15), suitable for separately connecting each respective reservoir (17) with the circuit (50),
 an electric pump (13) that reverses the pumping and backflow direction and effects continuous circulation in the circuit (50) of the solutions or liquid reagents taken from the reservoirs, and
 a sequential and coordinated control and command means (22) of the pump (13) and of the multipath solenoid valve (15), said control and command means being programmed to operate the multipath solenoid valve so as to separately connect each respective reservoir according to a predetermined sequence adapted to conduct fixation of molecules of biological origin or biomolecules on one or more samples within said containers,
 wherein said circuit (50) is capable of recycling at least part of one or more of the reagents originating from one or more of said reservoirs.

2. Installation according to claim 1, wherein the circuit (50) is a closed loop circuit for permanent recycling of the solutions or liquid reagents.

3. Installation according to claim 1, wherein the circuit (50) includes an open circuit for removal of one or more solutions or liquid reagents after at least one passage through the containers (1) in the casing.

4. Installation according to claim 1, wherein the containers (1) are stacked in the casing arranged vertically with the solutions or liquid reagents flowing upwards in the casing.

5. Installation according to claim 1, further comprising a second multipath solenoid valve (18) allowing either the recovery of at least some of the solutions or liquid reagents in order to cause them to circulate in a loop in the circuit (50) or the removal of these solutions or liquid reagents the recovery of at least some of the solutions or liquid reagents having circulated in the loop circuit (50), returned to their reservoirs (17) and removed from the latter to an external evacuation receptacle (21).

6. Installation according to claim 1, wherein the containers (1) are cylindrical and have the same height.

7. Installation according to claim 1, wherein the containers (1) have different heights.

8. Installation according to claim 1, wherein the containers (1), stacked in the casing, are immobilized between a fixed lower base (10), closing the casing, and a mobile upper base (11), the displacement of which inside the casing in order to be applied to the stack of containers, is controlled by an actuation piston (12) outside the casing, plunging into the latter and comprising an axial channel (8) for the circulation of the solutions or liquid reagents in the circuit (50).

9. Installation according to claim 8, wherein the mobile upper base (11) is equipped with a tight scraper (32), made of an appropriate elastic material, bearing against the internal surface of the casing.

10. Installation according to claim 1, wherein the side wall (3) of each of said containers (1) is transparent and made of a plastic material.

11. Installation according to claim 1, wherein the casing is made of glass or a transparent plastic material.

12. Installation according to claim 1, wherein the sequential control and command means (22) comprise a microcomputer which determines the composition, the order of flow in the circuit and the period for which the solutions or liquid reagents are brought into contact with the samples in the containers (1), as well as the flow rate of these solutions or liquid reagents.

13. Installation according to claim 1, wherein the casing is in a thermostatically controlled and thermoregulated enclosure (24).

14. Installation according to claim 13, wherein the thermostatically controlled enclosure (24) comprises a metallic strip (25), glued or otherwise applied to a generatrix of the casing, this strip being maintained in contact with a block of solid metal (26), against which is mounted an element (27) suitable for achieving controlled heating of this block.

15. Installation according to claim 14, wherein the circuit (50) comprises a coil (28) sealed in the metal block (26), placed in series in this circuit.

16. Installation according to claim 15, wherein the coil (28) is made of stainless steel and the metal block (26) of aluminum.

17. Installation according to claim 14, wherein the casing and the metallic strip (25) are surrounded by a protective cover (34).

18. Installation according to claim 1, wherein the casing is a tube.

* * * * *

UNITED STATES PATENT AND TRADEMARK OFFICE
CERTIFICATE OF CORRECTION

PATENT NO. : 8,425,862 B2  Page 1 of 1
APPLICATION NO. : 10/549146
DATED : April 23, 2013
INVENTOR(S) : Jacques Lucien Thelu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1762 days.

Signed and Sealed this
Eighth Day of September, 2015

Michelle K. Lee
*Director of the United States Patent and Trademark Office*